(12) United States Patent
Tornier et al.

(10) Patent No.: US 8,277,511 B2
(45) Date of Patent: Oct. 2, 2012

(54) SHOULDER OR HIP PROSTHESIS AND METHOD FOR SETTING SAME

(75) Inventors: Alain Tornier, Saint Ismier (FR); Irene Ferrari Epouse Gosset, Saint Vincent de Mercuze (FR)

(73) Assignee: Tornier SAS, Saint-Ismier (FR)

( * ) Notice: Subject to any disclaimer, the term of this patent is extended or adjusted under 35 U.S.C. 154(b) by 296 days.

(21) Appl. No.: 12/255,461

(22) Filed: Oct. 21, 2008

(65) Prior Publication Data

US 2009/0112328 A1    Apr. 30, 2009

Related U.S. Application Data

(63) Continuation of application No. PCT/FR2007/000670, filed on Apr. 20, 2007.

(30) Foreign Application Priority Data

Apr. 21, 2006  (FR) .................................... 06 03559

(51) Int. Cl.
   *A61F 2/30* (2006.01)
   *A61F 2/40* (2006.01)

(52) U.S. Cl. ................ 623/18.11; 623/19.11; 623/19.12

(58) Field of Classification Search ............... 623/18.11, 623/19.11–19.14; A61F 2/30, 2/40
   See application file for complete search history.

(56) References Cited

U.S. PATENT DOCUMENTS

| | | | |
|---|---|---|---|
| 3,694,820 A | 10/1972 | Scales et al. | |
| 3,815,157 A | 6/1974 | Skorecki et al. | |
| 3,842,442 A | 10/1974 | Kolbel | |
| 3,864,758 A | 2/1975 | Yakich | |
| 3,869,730 A | 3/1975 | Skobel | |
| 3,916,451 A | 11/1975 | Buechel et al. | |
| 3,978,528 A | 9/1976 | Crep | |
| 3,979,778 A | 9/1976 | Stroot | |
| 3,992,726 A | 11/1976 | Freeman et al. | |
| 4,003,095 A | 1/1977 | Gristina | |
| 4,030,143 A | 6/1977 | Elloy et al. | |
| 4,040,131 A | 8/1977 | Gristina | |
| 4,054,955 A | 10/1977 | Seppo | |
| 4,135,517 A | 1/1979 | Reale | |
| 4,179,758 A | 12/1979 | Gristina | |

(Continued)

FOREIGN PATENT DOCUMENTS

CH     426096     12/1966

(Continued)

OTHER PUBLICATIONS

"Aequalis-Fracture Suture Technique in 5 Steps," Tornier, Inc., 2 pp.

(Continued)

*Primary Examiner* — Thomas J Sweet
*Assistant Examiner* — Jason-Dennis Stewart
(74) *Attorney, Agent, or Firm* — Faegre Baker Daniels LLP (57) ABSTRACT

A prosthesis and method for a ball and socket joint. The prosthesis includes a first component including an anchoring shank and a metaphyseal portion. The metaphyseal portion includes a first articular surface configured to move in translation relative to the anchoring shank. An intermediate component includes a first articular surface configured to engage with the first articular surface on the metaphyseal portion, and a second articular surface configured to engage with the ball and socket joint.

16 Claims, 2 Drawing Sheets

U.S. PATENT DOCUMENTS

| | | | |
|---|---|---|---|
| 4,198,713 A | 4/1980 | Swanson | |
| 4,206,517 A | 6/1980 | Pappas et al. | |
| 4,261,062 A | 4/1981 | Amstutz et al. | |
| 4,550,450 A | 11/1985 | Kinnett | |
| 4,693,723 A | 9/1987 | Gabard | |
| 4,822,370 A | 4/1989 | Schelhas | |
| 4,846,840 A | 7/1989 | Leclercq et al. | |
| 4,865,605 A | 9/1989 | Dines et al. | |
| 4,865,609 A | 9/1989 | Roche | |
| 4,892,549 A | 1/1990 | Figgie, III et al. | |
| 4,919,669 A * | 4/1990 | Lannelongue | 623/19.12 |
| 4,919,670 A | 4/1990 | Dale et al. | |
| 4,957,510 A | 9/1990 | Cremascoli | |
| 4,963,155 A | 10/1990 | Lazzeri et al. | |
| 5,032,132 A | 7/1991 | Matsen, III et al. | |
| 5,080,673 A | 1/1992 | Burkhead et al. | |
| 5,080,685 A | 1/1992 | Bolesky et al. | |
| 5,127,920 A | 7/1992 | MacArthur | |
| 5,135,529 A | 8/1992 | Paxson et al. | |
| 5,163,961 A | 11/1992 | Harwin | |
| 5,171,289 A | 12/1992 | Tornier | |
| 5,181,928 A | 1/1993 | Bolesky et al. | |
| 5,192,329 A | 3/1993 | Christie et al. | |
| 5,201,882 A | 4/1993 | Paxson | |
| 5,206,925 A | 4/1993 | Nakazawa et al. | |
| 5,222,984 A | 6/1993 | Forte | |
| 5,261,914 A | 11/1993 | Warren | |
| 5,314,479 A | 5/1994 | Rockwood, Jr. et al. | |
| 5,314,485 A | 5/1994 | Judet | |
| 5,314,487 A | 5/1994 | Schryver et al. | |
| 5,326,359 A | 7/1994 | Oudard | |
| 5,330,531 A | 7/1994 | Capanna | |
| 5,358,526 A | 10/1994 | Tornier | |
| 5,383,936 A | 1/1995 | Kubein-Meesenburg et al. | |
| 5,389,107 A | 2/1995 | Nassar | |
| 5,405,399 A | 4/1995 | Tornier | |
| 5,425,779 A | 6/1995 | Schlosser | |
| 5,429,639 A | 7/1995 | Judet | |
| 5,443,519 A | 8/1995 | Averill et al. | |
| 5,458,650 A | 10/1995 | Carret et al. | |
| 5,462,563 A | 10/1995 | Shearer et al. | |
| 5,505,731 A | 4/1996 | Tornier | |
| 5,507,817 A | 4/1996 | Craig et al. | |
| 5,507,818 A | 4/1996 | McLaughlin | |
| 5,507,824 A | 4/1996 | Lennox | |
| 5,549,682 A | 8/1996 | Roy | |
| 5,580,352 A | 12/1996 | Sekel | |
| 5,591,168 A | 1/1997 | Judet et al. | |
| 5,662,651 A | 9/1997 | Tornier et al. | |
| 5,676,702 A | 10/1997 | Ratron | |
| 5,702,447 A | 12/1997 | Walch et al. | |
| 5,702,457 A | 12/1997 | Walch et al. | |
| 5,702,478 A | 12/1997 | Tornier | |
| 5,702,486 A | 12/1997 | Craig et al. | |
| 5,723,018 A | 3/1998 | Cyprien et al. | |
| 5,728,161 A | 3/1998 | Camino et al. | |
| 5,741,335 A | 4/1998 | Gerber et al. | |
| 5,755,807 A | 5/1998 | Anstaett et al. | |
| 5,766,256 A | 6/1998 | Oudard et al. | |
| 5,800,551 A | 9/1998 | Williamson et al. | |
| 5,824,106 A | 10/1998 | Fournol | |
| 5,879,395 A | 3/1999 | Tornier et al. | |
| 5,879,405 A | 3/1999 | Ries et al. | |
| 5,902,340 A | 5/1999 | White et al. | |
| 5,910,171 A | 6/1999 | Kummer et al. | |
| 5,928,285 A | 7/1999 | Bigliani | |
| 5,944,758 A | 8/1999 | Mansat et al. | |
| 5,961,555 A | 10/1999 | Huebner | |
| 5,984,927 A | 11/1999 | Wenstrom, Jr. et al. | |
| 6,015,437 A | 1/2000 | Stossel | |
| 6,033,439 A | 3/2000 | Camino et al. | |
| 6,045,582 A | 4/2000 | Prybyla | |
| 6,045,583 A | 4/2000 | Gross et al. | |
| 6,102,953 A | 8/2000 | Huebner | |
| 6,129,764 A | 10/2000 | Servfidio | |
| 6,162,254 A | 12/2000 | Timoteo | |
| 6,165,224 A | 12/2000 | Tornier | |
| 6,168,629 B1 | 1/2001 | Timoteo | |
| 6,171,341 B1 | 1/2001 | Boileau et al. | |
| 6,183,519 B1 | 2/2001 | Bonnin et al. | |
| 6,197,062 B1 | 3/2001 | Fenlin | |
| 6,197,063 B1 | 3/2001 | Dews | |
| 6,203,575 B1 | 3/2001 | Farey | |
| 6,206,925 B1 | 3/2001 | Tornier | |
| 6,228,120 B1 | 5/2001 | Leonard et al. | |
| 6,267,767 B1 | 7/2001 | Strobel et al. | |
| 6,283,999 B1 | 9/2001 | Rockwood, Jr. | |
| 6,299,646 B1 | 10/2001 | Chambat et al. | |
| 6,312,467 B1 | 11/2001 | McGee | |
| 6,328,758 B1 | 12/2001 | Tornier et al. | |
| 6,334,874 B1 | 1/2002 | Tornier et al. | |
| 6,364,910 B1 | 4/2002 | Shultz et al. | |
| 6,368,352 B1 | 4/2002 | Camino et al. | |
| 6,368,353 B1 | 4/2002 | Arcand | |
| 6,379,387 B1 | 4/2002 | Tornier | |
| 6,398,812 B1 | 6/2002 | Masini | |
| 6,406,495 B1 | 6/2002 | Schoch | |
| 6,406,496 B1 | 6/2002 | Ruter | |
| 6,436,144 B1 | 8/2002 | Ahrens | |
| 6,436,147 B1 | 8/2002 | Zweymuller | |
| 6,454,809 B1 | 9/2002 | Tornier | |
| 6,458,136 B1 | 10/2002 | Allard et al. | |
| 6,475,243 B1 | 11/2002 | Sheldon et al. | |
| 6,488,712 B1 | 12/2002 | Tornier et al. | |
| 6,494,913 B1 | 12/2002 | Huebner | |
| 6,506,214 B1 | 1/2003 | Gross | |
| 6,508,840 B1 | 1/2003 | Rockwood, Jr. et al. | |
| 6,514,287 B2 | 2/2003 | Ondrla et al. | |
| 6,520,994 B2 | 2/2003 | Nogarin | |
| 6,530,957 B1 | 3/2003 | Jack | |
| 6,540,770 B1 | 4/2003 | Tornier et al. | |
| 6,558,425 B2 | 5/2003 | Rockwood | |
| 6,569,202 B2 | 5/2003 | Whiteside | |
| 6,582,469 B1 | 6/2003 | Tornier | |
| 6,589,281 B2 | 7/2003 | Hyde, Jr. | |
| 6,599,295 B1 | 7/2003 | Tornier et al. | |
| 6,620,197 B2 | 9/2003 | Maroney et al. | |
| 6,626,946 B1 | 9/2003 | Walch et al. | |
| 6,673,114 B2 | 1/2004 | Hartdegen et al. | |
| 6,673,115 B2 | 1/2004 | Resch et al. | |
| 6,679,916 B1 | 1/2004 | Frankle et al. | |
| 6,736,851 B2 | 5/2004 | Maroney et al. | |
| 6,746,487 B2 | 6/2004 | Scifert et al. | |
| 6,749,637 B1 | 6/2004 | Bahler | |
| 6,755,866 B2 | 6/2004 | Southworth | |
| 6,761,740 B2 | 7/2004 | Tornier | |
| 6,767,368 B2 | 7/2004 | Tornier | |
| 6,780,190 B2 | 8/2004 | Maroney | |
| 6,783,549 B1 | 8/2004 | Stone et al. | |
| 6,790,234 B1 | 9/2004 | Frankle | |
| 6,802,864 B2 | 10/2004 | Tornier | |
| 6,824,567 B2 | 11/2004 | Tornier et al. | |
| 6,863,690 B2 | 3/2005 | Ball et al. | |
| 6,875,234 B2 | 4/2005 | Lipman et al. | |
| 6,887,277 B2 | 5/2005 | Rauscher et al. | |
| 6,890,357 B2 | 5/2005 | Tornier | |
| 6,890,358 B2 | 5/2005 | Ball et al. | |
| 6,942,699 B2 | 9/2005 | Stone et al. | |
| 6,953,478 B2 | 10/2005 | Bouttens et al. | |
| 6,969,406 B2 | 11/2005 | Tornier | |
| 7,011,686 B2 | 3/2006 | Ball et al. | |
| 7,033,396 B2 | 4/2006 | Tornier | |
| 7,066,959 B2 | 6/2006 | Errico | |
| 7,108,719 B2 | 9/2006 | Horber | |
| 7,166,132 B2 | 1/2007 | Callaway et al. | |
| 7,169,184 B2 | 1/2007 | Dalla Pria | |
| 7,175,663 B1 | 2/2007 | Stone | |
| 7,195,645 B2 | 3/2007 | Disilvestro et al. | |
| 7,238,207 B2 | 7/2007 | Blatter et al. | |
| 7,238,208 B2 | 7/2007 | Camino et al. | |
| 7,297,163 B2 | 11/2007 | Huebner | |
| 7,309,360 B2 | 12/2007 | Tornier et al. | |
| 7,329,284 B2 | 2/2008 | Maroney et al. | |
| 7,338,498 B2 | 3/2008 | Long et al. | |
| 7,338,528 B2 | 3/2008 | Stone et al. | |
| 7,468,077 B2 | 12/2008 | Rochetin | |
| 2001/0032021 A1 | 10/2001 | McKinnon | |

| | | | | | | |
|---|---|---|---|---|---|---|
| 2001/0047210 A1 | 11/2001 | Wolf | | 2007/0244564 A1 | 10/2007 | Ferrand et al. |
| 2001/0049561 A1 | 12/2001 | Dews et al. | | 2007/0250174 A1 | 10/2007 | Tornier et al. |
| 2001/0051831 A1 | 12/2001 | Subba Rao et al. | | 2007/0270718 A1 | 11/2007 | Rochetin et al. |
| 2002/0032484 A1 | 3/2002 | Hyde, Jr. | | | | |
| 2002/0099381 A1 | 7/2002 | Maroney | | | FOREIGN PATENT DOCUMENTS | |
| 2002/0138148 A1 | 9/2002 | Hyde, Jr. | | CH | 507704 | 5/1971 |
| 2002/0143402 A1 | 10/2002 | Steinberg | | DE | 3033227 | 4/1982 |
| 2002/0151982 A1 | 10/2002 | Masini | | DE | 19509037 | 9/1996 |
| 2003/0009170 A1 | 1/2003 | Tornier | | DE | 19630298 | 1/1998 |
| 2003/0009171 A1 | 1/2003 | Tornier | | EP | 0220803 | 5/1987 |
| 2003/0028198 A1 | 2/2003 | Tornier et al. | | EP | 0257359 | 8/1987 |
| 2003/0074072 A1 | 4/2003 | Errico et al. | | EP | 0299889 | 1/1989 |
| 2003/0097183 A1 | 5/2003 | Rauscher et al. | | EP | 0524857 | 1/1993 |
| 2003/0114933 A1 | 6/2003 | Bouttens et al. | | EP | 0549480 | 6/1993 |
| 2003/0149485 A1 | 8/2003 | Tornier | | EP | 0599429 | 6/1994 |
| 2003/0158605 A1 | 8/2003 | Tornier | | EP | 0617934 | 10/1994 |
| 2004/0002765 A1 | 1/2004 | Maroney et al. | | EP | 0664108 | 7/1995 |
| 2004/0006392 A1 | 1/2004 | Grusin et al. | | EP | 0679375 | 11/1995 |
| 2004/0030394 A1 | 2/2004 | Horber | | EP | 0712617 | 5/1996 |
| 2004/0034431 A1 | 2/2004 | Maroney et al. | | EP | 0715836 | 6/1996 |
| 2004/0039449 A1* | 2/2004 | Tornier ............... 623/19.13 | | EP | 0797964 | 10/1997 |
| 2004/0064189 A1 | 4/2004 | Maroney et al. | | EP | 0807426 | 11/1997 |
| 2004/0064190 A1 | 4/2004 | Ball et al. | | EP | 0809986 | 12/1997 |
| 2004/0133276 A1 | 7/2004 | Lang et al. | | EP | 0850609 | 7/1998 |
| 2004/0134821 A1 | 7/2004 | Tornier | | EP | 0864306 | 9/1998 |
| 2004/0138754 A1 | 7/2004 | Lang et al. | | EP | 0903127 | 3/1999 |
| 2004/0148033 A1 | 7/2004 | Schroeder | | EP | 0903128 | 3/1999 |
| 2004/0193276 A1 | 9/2004 | Maroney et al. | | EP | 0927548 | 7/1999 |
| 2004/0193277 A1 | 9/2004 | Long et al. | | EP | 1062923 | 12/2000 |
| 2004/0193278 A1 | 9/2004 | Maroney et al. | | EP | 1064890 | 1/2001 |
| 2004/0210220 A1 | 10/2004 | Tornier | | EP | 1195149 | 10/2002 |
| 2004/0210317 A1 | 10/2004 | Maroney et al. | | EP | 1380274 | 1/2004 |
| 2004/0215200 A1 | 10/2004 | Tornier et al. | | EP | 1402854 | 3/2004 |
| 2004/0220673 A1 | 11/2004 | Pria | | EP | 1543801 | 6/2005 |
| 2004/0220674 A1 | 11/2004 | Pria | | EP | 1611872 | 1/2006 |
| 2004/0225367 A1 | 11/2004 | Glien et al. | | FR | 2248820 | 5/1975 |
| 2004/0230197 A1 | 11/2004 | Tornier et al. | | FR | 2545352 | 11/1984 |
| 2004/0267370 A1 | 12/2004 | Ondrla | | FR | 2574283 | 6/1986 |
| 2005/0008672 A1 | 1/2005 | Winterbottom et al. | | FR | 2652498 | 4/1991 |
| 2005/0015154 A1 | 1/2005 | Lindsey et al. | | FR | 2664809 | 1/1992 |
| 2005/0043805 A1 | 2/2005 | Chudik | | FR | 2699400 | 6/1994 |
| 2005/0049709 A1 | 3/2005 | Tornier | | FR | 2712180 | 5/1995 |
| 2005/0055102 A1 | 3/2005 | Tornier et al. | | FR | 2770771 | 5/1995 |
| 2005/0065612 A1 | 3/2005 | Winslow | | FR | 2721200 | 12/1995 |
| 2005/0085919 A1 | 4/2005 | Durand-Allen et al. | | FR | 2726994 | 5/1996 |
| 2005/0085921 A1 | 4/2005 | Gupta et al. | | FR | 2737107 | 1/1997 |
| 2005/0090902 A1 | 4/2005 | Masini | | FR | 2835425 | 8/2003 |
| 2005/0107882 A1 | 5/2005 | Stone et al. | | FR | 2836039 | 8/2003 |
| 2005/0113931 A1 | 5/2005 | Horber | | FR | 2841768 | 1/2004 |
| 2005/0119531 A1 | 6/2005 | Sharratt | | SU | 749392 | 7/1980 |
| 2005/0143829 A1 | 6/2005 | Ondria et al. | | WO | WO 84/04668 | 12/1984 |
| 2005/0165490 A1 | 7/2005 | Tornier | | WO | WO 91/04718 | 4/1991 |
| 2005/0177241 A1 | 8/2005 | Angibaud et al. | | WO | WO 91/07932 | 6/1991 |
| 2005/0197708 A1 | 9/2005 | Stone et al. | | WO | WO 93/09733 | 5/1993 |
| 2005/0203536 A1 | 9/2005 | Laffargue et al. | | WO | WO 96/17553 | 6/1996 |
| 2005/0209700 A1 | 9/2005 | Rockwood et al. | | WO | WO 98/46172 | 10/1998 |
| 2005/0216092 A1 | 9/2005 | Marik et al. | | WO | WO 99/49792 | 10/1999 |
| 2005/0251263 A1 | 11/2005 | Forrer et al. | | WO | WO 99/65413 | 12/1999 |
| 2005/0256584 A1 | 11/2005 | Farrar | | WO | WO 00/15154 | 3/2000 |
| 2005/0267590 A1 | 12/2005 | Lee | | WO | WO 00/41653 | 7/2000 |
| 2005/0278030 A1 | 12/2005 | Tornier et al. | | WO | WO 01/47442 | 7/2001 |
| 2005/0278031 A1 | 12/2005 | Tornier et al. | | WO | WO 02/39931 | 5/2002 |
| 2005/0278032 A1 | 12/2005 | Tornier et al. | | WO | WO 02/39933 | 5/2002 |
| 2005/0278033 A1 | 12/2005 | Tornier et al. | | WO | WO 02/067821 | 9/2002 |
| 2005/0288681 A1 | 12/2005 | Klotz et al. | | WO | WO 03/005933 | 1/2003 |
| 2005/0288791 A1 | 12/2005 | Tornier et al. | | WO | WO 03/094806 | 11/2003 |
| 2006/0004462 A1 | 1/2006 | Gupta | | WO | WO 2007/109319 | 2/2007 |
| 2006/0009852 A1 | 1/2006 | Winslow et al. | | WO | WO 2007/109291 | 9/2007 |
| 2006/0015185 A1 | 1/2006 | Chambat et al. | | WO | WO 2007/109340 | 9/2007 |
| 2006/0020344 A1 | 1/2006 | Schultz et al. | | | | |
| 2006/0030946 A1 | 2/2006 | Ball et al. | | | OTHER PUBLICATIONS | |
| 2006/0173457 A1 | 8/2006 | Tornier | | | | |
| 2006/0235538 A1 | 10/2006 | Rochetin et al. | | | | |
| 2006/0241775 A1 | 10/2006 | Buss | | | | |
| 2007/0173947 A1 | 7/2007 | Ratron et al. | | | | |
| 2007/0179628 A1 | 8/2007 | Rochetin | | | | |
| 2007/0225817 A1 | 9/2007 | Reubelt et al. | | | | |
| 2007/0225818 A1 | 9/2007 | Reubelt et al. | | | | |
| 2007/0225821 A1 | 9/2007 | Reubelt et al. | | | | |

"Aequalis-Fracture Shoulder Prosthesis—Surgical Technique," Tornier, Inc., 32 pp.
"Aequalis® Press-Fit Shoulder Prosthesis—Surgical Technique," Tornier, Inc., 27 pp.
"Anatomical Shoulder™—Cemented Shoulder Prosthesis Product Information and Surgical Technique," Sulzer Medica, 2000, 30 pp.
"Anatomical Shoulder™ System Surgical Technique—Removable head option for improved surgical results," Zimmer, Inc., 2004, 33 pp.
Bigliani/Flatow®—The Complete Shoulder Solution, 4-Part Fracture of the Humerus Surgical Technique, Zimmer, Inc., 2000, 18 pp.
"Bio-Modular® / Bi-Polar Shoulder Arthroplasty," Biomet, Inc., 1997, 2 pp.
"Bio-Modular® Choice, Shoulder System," Biomet Orthopedics, Inc., 2004, 16 pp.
"Bio-Modular Total Shoulder Surgical Technique," Biomet Orthopedics, Inc., 2001, 12 pp.
"Copeland™ Humeral Resurfacing Head," Biomet Orthopedics, Inc., 2001, 12 pp.
"Global C.A.P. ™ Surgical technique, resurfacing humeral head implant," DePuy International, Ltd., 2004, 23 pp.
Boileau, et al. "Adaptability and modularity of shoulder prosthese," Maitrise Orthopédique, https://www.maitriseorthop.com/corpusmaitri/orthopaedic/prothese_epaule_orthop/boileau_us.shtml, Jan. 3, 2006, 14 pp.
Boileau, et al. "Arthroscopic Repair of Full-Thickness Tears of the Supraspinatus: Does the tendon really heal?," *The Journal of Bone and Joint Surgery*, Inc., pp. 1229-1240, 2005, 12 pp.
"Design Rationale," Latitude®, undated, 36 pp.
Klein et al. "Mechanically favorable bone remodeling in rotator cuff arthropathy patients with good function," *Minneapolis Sports Medicine Center and University of Minnesota*, 2 pp.
Mansat, "Neer 3™, Surgical Technique for Fractures," Smith & Nephew, 2000, 19 pp.
Molé, M.D. et al., "Aequalis-Reversed™ Shoulder Prosthesis, Surgical Technique," Tornier, Inc., 24 pp.
Nicholson, "Arthroplasty and Rotator Cuff Deficiency," Chapter 7, pp. 149-166.
"Offset Head, Bio-Modular® Total Shoulder," Biomet, Inc. 2000, 2 pp.
"The FOUNDATION® Total Shoulder System," Encore Surgical, undated, 2 pp.
"The Townley Modular Shoulder, Design by Reason," Biopro, Inc., 2 pp.
Zimmer® Bigliani/Flatow®—The Complete Shoulder Solution, Total Shoulder Arthroplasty Surgical Technique, Zimmer, Inc., 2003, 30 pp.
"Zimmer® Shoulder Retractors,"Zimmer, Inc., 2000, 2 pp.

"Anatomic Glenoid, Surgical Technique," Smith & Nephew, 2000, 6 pp.
"Anatomical Shoulder™ System—The new removable head option," Zimmer Inc., 2004, 6 pp.
"Delta CTA™ Reverse Shoulder Prosthesis," DePuy International, Ltd., 2004, 28 pp.
Cofield, M.D., "Cofield[2] Total Shoulder System, Surgical Technique," Smith & Nephew, 1997, 32 pp.
"Aequalis®-Glenoid Keeled and Pegged—Surgical Technique," Tornier, Inc., undated, 12 pp.
"Bigliani/Flatow®—The Complete Shoulder Solution, Designed by Shoulder Surgeons for Shoulder Surgery," Zimmer, Inc., 2001, 6 pp.
"Tornier Surgical Technique Addendum, Tornier Aequalis® Reversed Hemi-Adaptor Technique," Tornier, Inc., Aug. 8, 2005, 1 pg.
"Tornier Surgical Technique Addendum, Aequalis® Reversed Shoulder Polyethylene Insert," Tornier, Inc., Aug. 8, 2005, 1 pg.
Fenlin, M.D., Symposium Surgery of the Shoulder, "Total Glenohumeral Joint Replacement," Orthopedic Clinics of North America 6(2):565-583, Apr. 1975.
Search Report from French application No. PCT/FR2007/000670, mailed Aug. 1, 2008, 4 pp.
Beuchel, M.D., "Beuchel-Pappas™ Modular Salvage Shoulder System," Endotec, Inc., 2000, 8 pp.
Beuchel, M.D., "Beuchel-Pappas™ Resurfacing Shoulder System," Endotec, Inc., 2000, 8 pp.
Beuchel, M.D., "Beuchel-Pappas™ Total Shoulder System," Endotec, Inc., 2000, 16 pp.
Hertel, M.D., PD, "Technical considerations for implantation of EPOCA glenoid components (Leseprobe)," *Epoca Newsletter*, May 14, 2001, 1 pg.
Apoil, "A Condyle for the Rotator Cuff Muscles, the total shoulder prosthesis," Aesculap®, 1994, 4 pp.
"Tornier Aequalis® Reversed 2 Prong Capsular Retractor," Tornier, Inc., Oct. 8, 2005.
"Tornier Aequalis® Reversed Shoulder G2 Baseplate," Tornier, Inc., Oct. 8, 2005.
Boileau et al., U.S. Appl. No. 12/020,913, entitled "Method and Apparatus for Fitting a Shoulder Prosthesis" filed Jan. 28, 2008.

* cited by examiner

SHOULDER OR HIP PROSTHESIS AND METHOD FOR SETTING SAME

CROSS REFERENCE TO RELATED APPLICATIONS

This application is a continuation of International Application No. PCT/FR2007/000670, with an international filing date of Apr. 20, 2007, entitled Shoulder or Hip Prosthesis and Method for Setting Same (Prothese D'Epaule Ou De Hanche Et Methode De Pose D'Une Telle Prothese), which claims priority to French application No. 0603559, filed Apr. 21, 2006, the disclosures of which are all hereby incorporated by reference.

FIELD OF THE INVENTION

The present invention relates to a shoulder or hip prosthesis.

BACKGROUND OF THE INVENTION

Within the field of shoulder prostheses, it is known, for example from FR-A-2 841 768, to use an intermediary component having two convex articulation surfaces designed to co-operate with a concave articulation surface belonging to the humeral component of the prosthesis and a concave glenoid articulation surface respectively. This type of prosthesis gives overall satisfaction, particularly since the distribution of the instantaneous centres of rotation of the articular surfaces in contact enables the point of application of the effort exerted by the deltoid during the abduction movement to be externalised. However, in some implantation configurations, the external part of the humeral component or the humerus risks coming into contact with the acromion, which may be irritating, or even painful, for the patient.

Similar problems may arise with a shoulder prosthesis that has a humeral component with a convex articulation surface, the intermediate component thus having a corresponding concave articulation surface. Problems of the same type may arise with a known hip prosthesis.

These are the drawbacks that the invention more particularly aims to remedy by proposing a new shoulder prosthesis in which the abduction effort exerted by the deltoid can be optimised, without risking interaction between the humerus or humeral component and the acromion at the end of the abduction movement. The invention also proposes a hip prosthesis.

BRIEF SUMMARY OF THE INVENTION

For this purpose, the invention relates to a shoulder or hip prosthesis which comprises a humeral or femoral component having an articulation surface and an intermediate component having a first and second articulation surface designed to co-operate with the articulation surface of the humeral or femoral component respectively and with a concave articulation surface which is natural or belongs to a glenoid or cotyloid component, the humeral component comprising a first part designed to be anchored in the humerus or in the femur. This prosthesis is characterised in that the articulation surface of the humeral or femoral component is formed by a second part of this component which is movable in translation in relation to the first part in a moving-away/approaching direction between the first part and the articulation surface of the humeral or femoral component.

In the case of a shoulder prosthesis, the possibility of relative movement in translation between the first and second parts of the humeral component makes it possible to vary, during the abduction movement, the lever arm between the point of application of the effort due to the deltoid and the instantaneous centre of rotation of the surfaces in contact located on the humeral component and on the intermediate component respectively. This lever arm can therefore be thinner at the end of abduction, which limits the risks of interference of the humerus or humeral component with the acromion. In the case of a hip prosthesis, similar advantages are obtained on elevating the patient's leg.

One embodiment is directed to a prosthesis for a ball and socket joint. The prosthesis includes a first component including an anchoring shank and a metaphyseal portion. The metaphyseal portion includes a first articular surface configured to move in translation relative to the anchoring shank. An intermediate component includes a first articular surface configured to engage with the first articular surface on the metaphyseal portion, and a second articular surface configured to engage with the ball and socket joint.

In one embodiment, a second component is provided that is adapted for implantation in a socket portion of the ball and socket joint. The second component includes a first articular surface adapted to engage with the second articular surface on the intermediate component. The second articular surface of the intermediate component is preferably unconstrained relative to the first articular surface on the second component.

In one embodiment the first articular surface on the metaphyseal portion includes a rod telescopically engaged with the metaphyseal portion. The rod preferably includes a non-circular cross-section. The first articular surface of the metaphyseal portion preferably moves in translation relative to the anchoring shaft in one degree of freedom.

The distance between the first articular surface and the metaphyseal portion decreases with abduction of the ball and socket joint. The center of rotation of the first articular surface on the metaphyseal portion is typically located inside the ball and socket joint. The lever arm of the ball and socket joint typically decreases in abduction. In one embodiment, the prosthesis includes end stops on the intermediate component and the metaphyseal portion limiting abduction of the ball and socket joint.

In one embodiment, the first articular surface on the metaphyseal portion is concave, and at least the first articular surface on the intermediate component is convex. In another embodiment, the first articular surface on the metaphyseal portion is convex, and at least the first articular surface on the intermediate component is concave. In another embodiment, the ball and socket joint is a shoulder joint and the anchoring shank is adapted to connect to a medullary cavity of a humerus.

Another embodiment is directed to a prosthesis for a shoulder joint. A first component includes an anchoring shank adapted to connect to a medullary cavity of a humerus, and a metaphyseal portion. A first articular surface coupled to the metaphyseal portion is configured to move in translation relative to the anchoring shank. An intermediate component includes a first articular surface configured to engage with the first articular surface on the metaphyseal portion, and a second articular surface configured to engage with a glenoid cavity of the shoulder joint. In one embodiment, a second component adapted for implantation in a glenoid cavity of the shoulder joint is provided. The second component includes a first articular surface adapted to engage with the second articular surface on the intermediate component.

The present invention is also directed to a method of fitting a prosthesis in a shoulder joint. The method includes connecting an anchoring shaft of a first component to a medullary cavity of a humerus. A first articular surface is coupled to a metaphyseal portion of the first component to move in translation relative to the anchoring shank. An intermediate component is located between a glenoid cavity of the shoulder joint and the first articular surface. A first articular surface on the intermediate component is engaged with the first articular surface on the metaphyseal portion. A second articular surface on the intermediate component is engaged with the glenoid cavity of the shoulder joint.

In one embodiment, the method includes implanting a second component in the glenoid cavity and engaging a first articular surface on the second component with the second articular surface on the intermediate component. In another embodiment, a distance between the first articular surface and the metaphyseal portion is reduced during abduction of the shoulder joint.

According to the advantageous but not obligatory features of the invention, such a prosthesis may incorporate one or more additional.

For example, the second part of the humeral or femoral component has an assembly rod on the first part, such rod forming part of a telescopic structure to guide the translation movement between the first and second parts of this component. According to a first embodiment, the rod may be engaged in a guide bore formed by or connected to the first part. According to another embodiment, the rod is hollow and adapted to receive, with the possibility of sliding, a finger which projects in relation to the first part. Furthermore, the rod and the supplementary part of the telescopic structure advantageously have a non-circular cross-section.

End stops are provided to the relative translation movement of the first and second parts of the humeral component in an approaching direction between the first part and the intermediate component.

According to a first type of prosthesis according to the invention, the articulation surface of the humeral or femoral component is concave, whereas the first and second articulation surfaces of the intermediate component are convex. According to another type of prosthesis according to the invention, the articulation surface of the humeral or femoral component is convex, whereas the first and second articulation surfaces of the intermediate component are concave and convex respectively.

The invention also relates to a method of fitting a shoulder or hip prosthesis as previously described and, more precisely, a method of fitting a prosthesis that comprises a humeral or femoral component, of which a first part is designed to be anchored in the humerus or the femur and which has an articulation surface and an intermediate component that have a first and second articulation surface designed to co-operate with the articulation surface of the humeral or femoral component respectively and with a concave articulation surface which is natural or belongs to a glenoid or cotyloid component, this method comprising a stage consisting in fitting a second part of the humeral or femoral component, which forms its articulation surface, in a sliding manner onto the first part.

BRIEF DESCRIPTION OF THE SEVERAL VIEWS OF THE DRAWING

Further features and advantages of the invention will emerge more clearly from the following description of three embodiments of a prosthesis according to its principle, given purely by way of example and made with reference to the accompanying drawings in which.

DETAILED DESCRIPTION OF THE INVENTION

Figures 1, 2, 3:
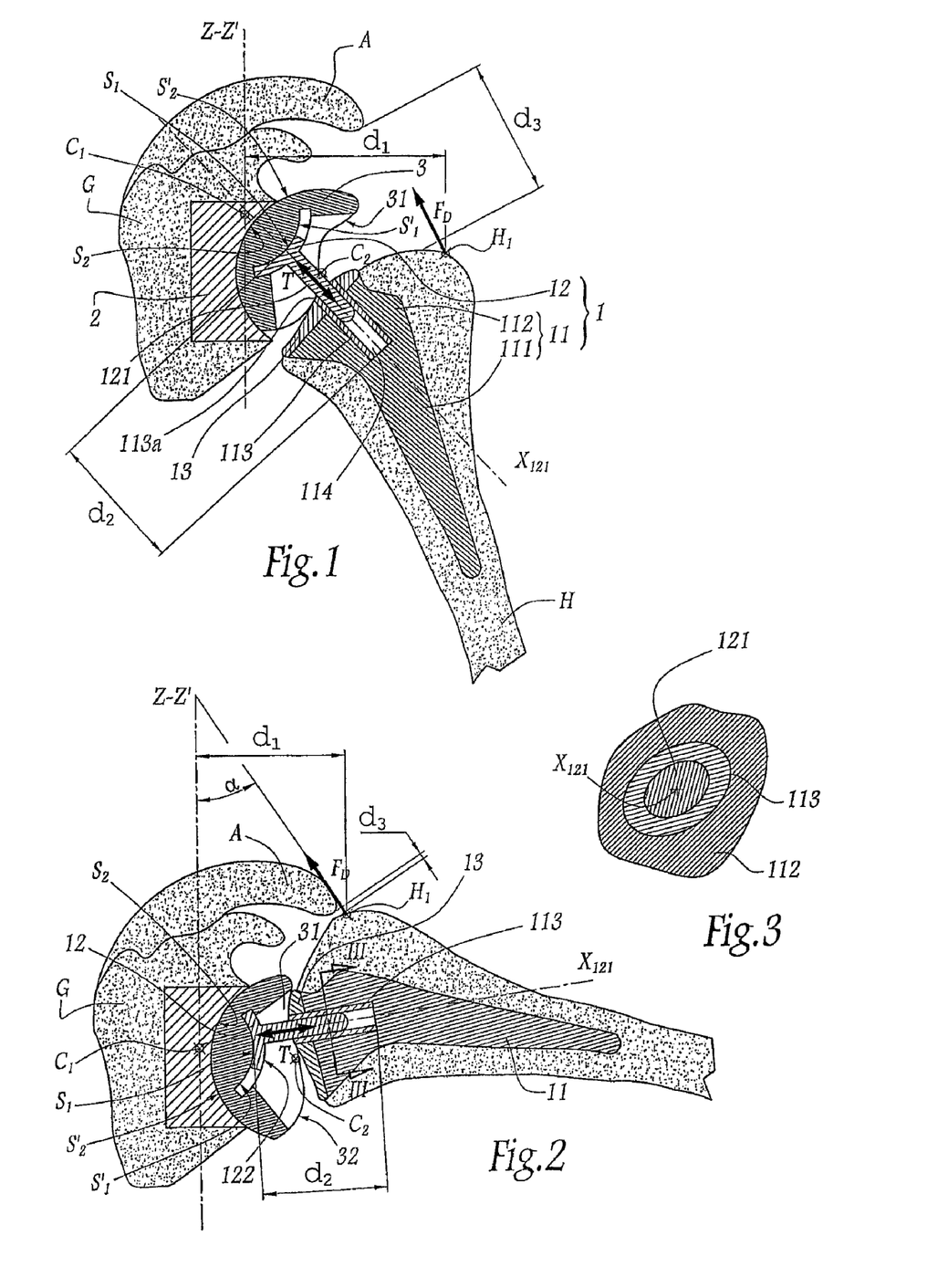
FIG. 1 is a sectional view of a prosthesis in according with an embodiment of the present invention shown in a patient's arm at the start of an abduction movement.
FIG. 2 is a sectional view of the prosthesis of FIG. 1 shown at the end of an abduction.
FIG. 3 is a partial section of the prosthesis of FIG. 1 along line III-III in FIG. 2.

The prosthesis P shown in FIGS. 1 to 3 comprises a humeral component 1 which includes a part 11 designed to be anchored in the medullary canal of the humerus H of the joint to be fitted with the prosthesis P. Part 11 comprises an anchoring shank 111 and a metaphyseal part 112 in which a tube 113 with an oval internal section is fixed, as can be seen more clearly in FIG. 3. The component 1 also comprises a pad 12 which defines a concave surface $S_1$ and is fitted, opposite the surface $S_1$, with a rod 121 with an oval section that is complementary to the inner section of the tube 113.

In the mounted configuration of the prosthesis, the concavity of the surface $S_1$ is facing towards the glenoid G of the shoulder.

The prosthesis P also comprises a glenoid component 2 anchored in the glenoid G and defining a concave surface $S_2$ whose concavity is turned towards the exterior of the glenoid. Between the components 1 and 2, an intermediate component 3 is inserted which defines an external convex surface $S'_2$ which is substantially complementary to surface $S_2$, as well as a surface $S'_1$ which is also convex and substantially complementary to surface $S_1$. The surface $S'_2$ of the intermediate component 3 is preferably unconstrained relative to the surface $S_2$.

In the embodiment described, the surfaces $S_1$, $S_2$, $S'_1$ and $S'_2$ are sections of a sphere, the radius $R_1$ common to surfaces $S_1$ and $S'_1$ being smaller than the radius $R_2$ common to surfaces $S_2$ and $S'_2$. However, surfaces $S_1$, $S_2$, $S'_1$ and $S'_2$ are not necessarily sections of a sphere.

The relative position of surfaces $S_1$, $S_2$, $S'_1$ and $S'_2$ is in accordance with the technical disclosure of FR-A-2 841 768. Note that $C_1$ is the instantaneous centre of rotation of surface $S_1$ in relation to surface $S'_1$. It is a centre common to the spheres defining the surfaces $S_1$ and $S'_1$. The geometry of elements 2, 3 and 12 is such that the centre $C_1$ is situated in the glenoid bone G, that is, in a median position in relation to the anatomical centre of rotation of the shoulder before operation.

Note also that $C_2$ is the instantaneous centre of rotation between surfaces $S_2$ and $S'_2$. In this embodiment, it is the centre common to the spheres defining these surfaces. It is situated beyond the surface $S'_1$ in relation to surface $S_2$, which is in accordance with the technical disclosure of FR-A-2 841 768. Commonly assign U.S. Pat. No. 7,033,396 and U.S. Patent Publication Nos. 2005/0288791 and 2005/0165490 are hereby incorporated by reference.

Note that $H_1$ is the point of the humerus H at which the resultant force of the effort $F_D$ of the deltoid is applied during the abduction movement of the humerus.

Note that Z-Z' is an axis that is globally parallel to the vertebral column of the patient when standing and passes through the centre $C_1$. Note that $d_1$ is the distance, measured perpendicularly to the axis Z-Z', between point $H_1$ and the centre $C_1$. This distance $d_1$ constitutes the lever arm of the effort $F_D$ that causes the movement of the surface $S_1$ of the pad 12 on the surface $S'_1$ during abduction. The longer this lever arm, the easier it is for the patient to lift his arm as a result of the effort $F_D$ exerted by the deltoid, which is particularly great if the rotator cuff, which holds down the humeral head, is deficient.

In order to prevent point $H_1$ or a region of the humerus close to this point from impinging on the acromion A at the end of the abduction movement, the rod 121 slides inside the tube 113, which makes it possible to vary the distance $d_2$ between the surface $S_1$ and the bottom of the bore 114 made in the part 112 in order to receive the tube 113, this distance $d_2$ being measured parallel to the central longitudinal axis $X_{121}$ of the rod 121. The axis $X_{121}$ is also the central axis of the tube 113.

Thus, the pad 12 is movable in translation away from/approaching part 11, in the direction of the double arrow T and parallel to axis $X_{121}$. The translation movement of the pad 12 in relation to the part 13 corresponds to an approach of part 11, on the one hand, and of the elements 12 and 3 resting on each other, on the other, during abduction. By contrast, when the patient lowers his arm, elements 12 and 3, on the one hand, and 11, on the other, move away from each other.

In other words, the rod 121 can slide inside the tube 113, which forms a bore that guides the rod in translation, so that the distance $d_2$ is variable, as a comparison between FIGS. 1 and 2 shows. The variable nature of distance $d_2$ also results in the distance $d_1$ having a variable nature. In the configuration shown in FIG. 2, the distance $d_1$ is shorter than it is in the configuration shown in FIG. 1. This is not problematic since, when the humerus is near the configuration shown in FIG. 2 or in this configuration at the end of the abduction movement, the resultant $F_D$ of the effort due to the deltoid forms an angle α, with the axis Z-Z', which is substantially greater than in the configuration shown in FIG. 1, so that this resultant force then tends to draw the top of the prosthesis towards the glenoid G, which limits the risks of luxation (e.g., displacement or misalignment of a joint). Thus, at the end of the abduction movement, the distance between the humerus H and the acromion A is not zero, although less than it was at the start in the configuration shown in FIG. 1.

Thus, the telescopic structure formed by the rod 121 and the tube 113 allows the lever arm $d_1$ of the resultant $F_D$ to be adapted to the position of the humerus H during the abduction movement. At the start of the movement shown in FIG. 1, this distance or lever arm $d_1$ is maximum, which facilitates abduction, whereas, at the end of the movement, this distance or lever arm is minimum, which prevents interference with the acromion.

As shown more clearly in FIG. 3, the rod 121 and the tube 113 have complementary non-circular sections, which enables the angular position of the pad 12 to be restrained about the axis $X_{121}$. The non-circular cross-sections constrain movement of the rod 121 in the tube 113 to one degree of freedom. In an alternate embodiment, the rod 121 and tube 113 have circular cross-sections, permitting rotation of the pad 12 relative to the metaphyseal part 112. In this alternate embodiment, the pad 12 is permitted to move in two degrees of freedom.

Furthermore, a plug 13, inserted in the humerus H around the part of the tube 113 which projects in relation to the metaphyseal part 112, comes in abutment against a corresponding portion 31 of the component 3 at the end of the abduction movement in order to limit the approach of parts 11 and 12. Parts 13 and 31 thus form a stop to the approaching movement of parts 11 and 12 during abduction.

In a variant, the end 113a of the tube 113 opposite the shank 111 can come to a stop against the rear face 122 of the pad 12, that is the face of this pad opposite the surface $S_1$. The abutment of the end 113a against the face 122 thus forms a stop to the approaching movement of parts 11 and 12.

According to an optional feature of the invention, the edge 32 of the component 3 can receive the plug 13 in sliding bearing, the shape of this edge being compatible with an approach of the surface $S_1$ and part 11 during the adduction movement, as shown in FIGS. 1 and 2.

According to a feature of the invention which is not shown, a stop can also be provided, for example in the vicinity of the free end of the rod 121, to limit the distancing of parts 11 and 12 and thus prevent the extraction of the rod 121 in relation to the tube 113 in the configuration shown in FIG. 1.

Figure 4:
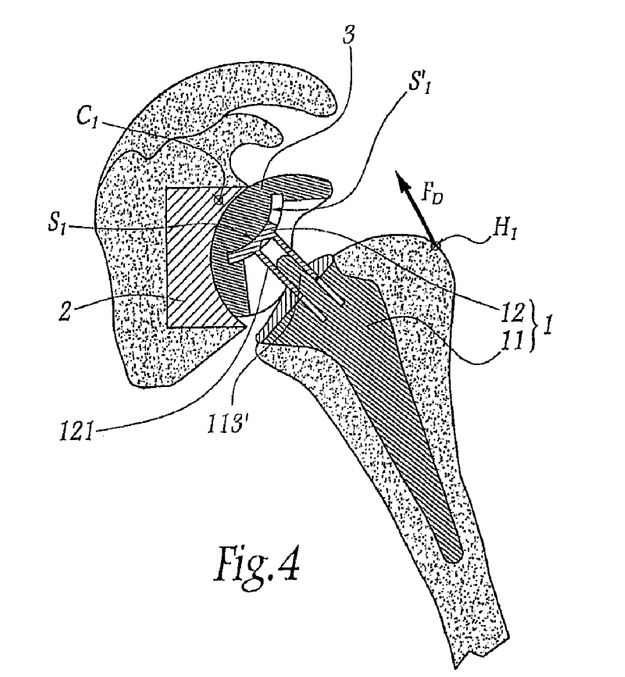
FIG. 4 is a section similar of an alternate prosthesis according to an embodiment of the present invention.

In the second embodiment of the invention shown in FIG. 4, elements similar to those of the first embodiment bear the same reference numerals. This embodiment differs from the preceding one substantially in that the rod 121 of the pad 12 is hollow and forms a bore to receive a finger 113' which projects in relation to part 11, in the direction of the pad 12. As before, a telescopic structure is formed which allows the lever arm to be adjusted between the point $H_1$ where the resultant $F_D$ of the effort due to the deltoid is exerted and the instantaneous centre of rotation $C_1$ of the concave surface $S_1$ formed by the pad 12 in relation to the corresponding convex surface $S'_1$ formed by the intermediate component 3.

As in the first embodiment, the elements 121 and 113' that make up the telescopic structure have a non-circular section. In this embodiment, they can have a polygonal section.

Figure 5:
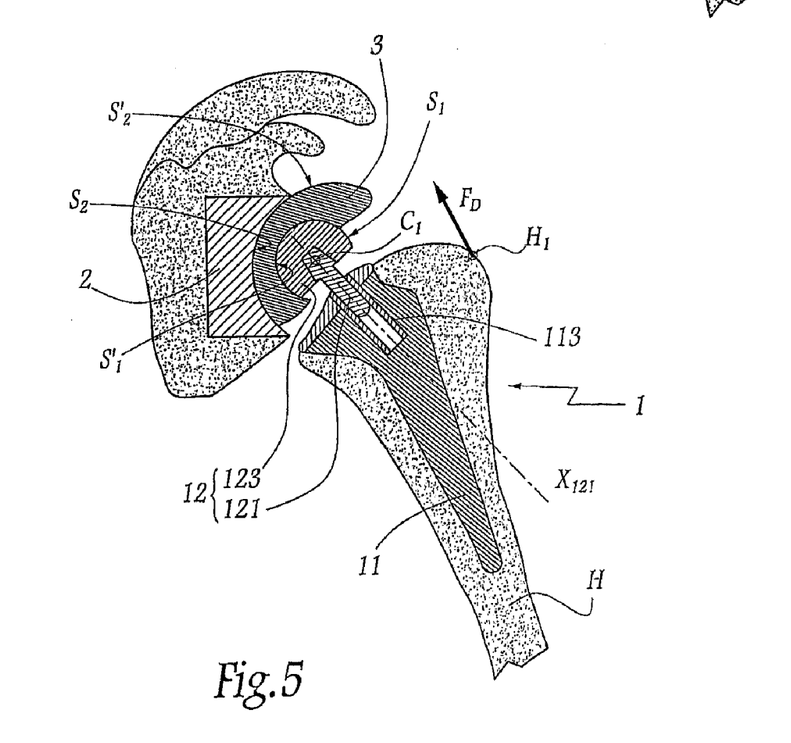
FIG. 5 is a section similar of another alternate prosthesis according to an embodiment of the present invention.

In the third embodiment of the invention shown in FIG. 5, elements similar to those shown in the first embodiment bear the same reference numerals. This embodiment differs from the preceding one in that the articulation surface $S_1$ of the humeral component is formed by a section of a sphere 123 mounted, using a Morse-taper type assembly, on a rod 121 similar to that of the first embodiment. The intermediate component 3 defines a concave articulation surface $S'_1$, in the form of a section of a sphere substantially complementary to the surface $S_1$, as well as a convex articulation surface $S'_2$ complementary to an articulation surface $S_2$ defined by the glenoid component 2 of the prosthesis P.

The rod 121 is mounted sliding in a tube 113 and can move within this tube, parallel to its longitudinal axis $X_{121}$.

Once assembled, parts 121 and 123 together form a pad 12 which is movable in translation in relation to part 11 of the prosthesis P anchored in the humerus H. The telescopic structure formed between elements 121 and 113 enables the lever arm to be adjusted between point $H_1$ where the resultant $F_D$ of the effort due to the deltoid is exerted and the instantaneous centre of rotation $C_1$ of the surface $S_1$ in relation to the surface $S'_1$.

As before, elements 121 and 123 can have a non-circular section.

When a prosthesis according to one of the previously-described embodiments is to be fitted, its part 11 is anchored in the humerus before the pad 12 is fitted onto this part 11, with the possibility of sliding, by engaging its rod 121 in the corresponding tube 113 for the first embodiment or the finger 113' in the rod 121 for the second embodiment. The pad 12 may be fitted onto part 11 before or after surface $S_1$ of this pad has been placed in contact with surface $S'_1$ of component 3.

In a variant, the pad 11 can be fitted onto part 12 before this part is anchored in the humerus.

According to a variant of the invention, not shown, the glenoid component 2 can be omitted and the surface $S'_2$ of component 3 rests against a natural glenoid surface.

The invention has been shown installed in shoulder prostheses. It is also applicable to hip prostheses of which the femoral component can have two parts that are movable in translation in relation to each other in a moving-away/approaching direction between the part designed to be anchored in the femur and its articulation surface.

Where a range of values is provided, it is understood that each intervening value, to the tenth of the unit of the lower limit unless the context clearly dictates otherwise, between the upper and lower limit of that range and any other stated or intervening value in that stated range is encompassed within the inventions. The upper and lower limits of these smaller ranges which may independently be included in the smaller ranges is also encompassed within the inventions, subject to any specifically excluded limit in the stated range. Where the stated range includes one or both of the limits, ranges excluding either both of those included limits are also included in the inventions.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present inventions are not entitled to antedate such publication by virtue of prior invention. Further, the dates of publication provided may be different from the actual publication dates which may need to be independently confirmed.

Other embodiments of the invention are possible. Although the description above contains many specificities, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims.

What is claimed is:

1. A prosthesis for a ball and socket joint, the prosthesis comprising:
    a first component including an anchoring shank and a metaphyseal portion, the metaphyseal portion comprising a translation portion defining a first articular surface, and a receiving portion configured to receive the translation portion in a complementary fit such that the translation portion is free to move in two directions relative to the anchoring shank in a first degree of freedom while constraining movement of the translation portion relative to the anchoring shank in a second degree of freedom; and
    an intermediate component comprising a first articular surface configured to engage with the first articular surface of the translation portion such that the intermediate component and the first component articulate between a first articular position and a second articular position, and a second articular surface configured to engage with the ball and socket joint, the first component and the intermediate component configured to engage with one another such that a distance between the first articular surface of the intermediate component and the metaphyseal portion decreases from the first articular position to the second articular position.

2. The prosthesis of claim 1 comprising a second component adapted for implantation in a socket portion of the ball and socket joint, the second component comprising a first articular surface adapted to engage with the second articular surface on the intermediate component.

3. The prosthesis of claim 2 wherein the second articular surface of the intermediate component is unconstrained relative to the first articular surface on the second component.

4. The prosthesis of claim 1 wherein the first articular surface on the metaphyseal portion comprises a rod telescopically engaged with the metaphyseal portion.

5. The prosthesis of claim 4 wherein the rod comprises a non-circular cross-section.

6. The prosthesis of claim 1 wherein the first articular surface of the metaphyseal portion moves in translation in one degree of freedom relative to the anchoring shank.

7. The prosthesis of claim 1 wherein a distance between the first articular surface and the metaphyseal portion decreases with abduction of the ball and socket joint.

8. The prosthesis of claim 1 wherein a center of rotation of the first articular surface on the metaphyseal portion is located inside the ball and socket joint.

9. The prosthesis of claim 1 wherein a lever arm of the ball and socket joint decreases in abduction.

10. The prosthesis of claim 1 comprising end stops on the intermediate component and the metaphyseal portion limiting abduction of the ball and socket joint.

11. The prosthesis of claim 1 wherein the first articular surface on the metaphyseal portion is concave, and at least the first articular surface on the intermediate component is convex.

12. The prosthesis of claim 1 wherein the first articular surface on the metaphyseal portion is convex, and at least the first articular surface on the intermediate component is concave.

13. The prosthesis of claim 1 wherein the second articular surface of the intermediate component is unconstrained relative to the ball and socket joint.

14. The prosthesis of claim 1 wherein the ball and socket joint is a shoulder joint and the anchoring shank is adapted to connect to a medullary cavity of a humerus.

15. A prosthesis for a shoulder joint, the prosthesis comprising:
- a first component comprising an anchoring shank adapted to connect to a medullary cavity of a humerus and a metaphyseal portion fixed to the anchoring shank;
- a translation portion defining a first articular surface and being slidably coupled to the metaphyseal portion such that the translation portion is configured to move in translation relative to the anchoring shank between a first position and a second position; and
- an intermediate component comprising a first articular surface configured to engage with the first articular surface of the translation portion, a second articular surface configured to engage with a glenoid cavity of the shoulder joint, and a third surface adapted to slide against the metaphyseal portion to form a stop that limits translational movement of the first component relative to the intermediate component during sliding of the translation portion relative to the metaphyseal portion between the first position and the second position.

16. The prosthesis of claim 15 comprising a second component adapted for implantation in a glenoid cavity of the shoulder joint, the second component comprising a first articular surface adapted to engage with the second articular surface on the intermediate component.

* * * * *